United States Patent [19]

Smith et al.

[11] Patent Number: 5,199,305
[45] Date of Patent: Apr. 6, 1993

[54] METHOD AND APPARATUS FOR MEASURING THE STRAIN DEVELOPED IN A COATED SURFACE

[75] Inventors: Sheldon M. Smith, Los Gatos; Clement C. Hiel, San Jose, both of Calif.

[73] Assignee: The United States of America as represented by the Administrator of National Aeronautics and Space Administration, Washington, D.C.

[21] Appl. No.: 779,672

[22] Filed: Oct. 21, 1991

[51] Int. Cl.$^5$ .............................................. G01N 3/20
[52] U.S. Cl. .................................. 73/851; 73/150 A; 73/827
[58] Field of Search .................... 73/827, 762, 150 A, 73/851

[56] References Cited

U.S. PATENT DOCUMENTS

| | | | |
|---|---|---|---|
| 2,310,845 | 2/1943 | Ellis | 73/762 |
| 2,645,935 | 7/1953 | Pramuk et al. | 73/851 X |
| 2,724,964 | 11/1955 | Singdale | 73/762 |
| 2,924,897 | 2/1960 | Ellis | 73/762 |
| 3,410,133 | 11/1968 | Savage | 73/851 X |
| 3,779,065 | 12/1973 | Ellis | 73/1 R |
| 4,413,510 | 11/1983 | McCusker et al. | 73/150 A |
| 4,506,547 | 3/1985 | Kunze et al. | 73/150 R |
| 4,856,326 | 8/1989 | Tsukamoto | 73/150 A |

Primary Examiner—Jerry W. Myracle
Attorney, Agent, or Firm—Darrell G. Brekke; Guy Miller; John R. Manning

[57] ABSTRACT

A method and apparatus are provided for determining the strain developed in a coated surface. A beam with a coating on a surface thereof is mounted as a cantilever and a force is applied to the free end of the beam to cause deflection of the beam until the coating on the beam fails. The strain in the beam, and hence in the coating at the point of failure, is determined based on the dimensions of the beam, the point along the beam where failure of the coating occurs and the amount of deflection of the beam, and this determination is made independently of the temperature of the beam and the material from which the beam is made. The determination is made based on the equation $E = 1.5hdx/l^3$, where E is strain, h is the beam thickness, d is the beam deflection, x is the distance from the free end of the beam to the point where failure of the coating occurred, and l is the length of the beam.

7 Claims, 1 Drawing Sheet

METHOD AND APPARATUS FOR MEASURING THE STRAIN DEVELOPED IN A COATED SURFACE

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION a. Technical Field of the Invention

The present invention relates to the measurement of strain in a coated surface and, more particularly, to a method and apparatus which enables such a measurement to be made under realistic thermal and mechanical loads.

b. Description of the Prior Art

Several Standard Test Methods of the American Society for Testing and Materials (ASTM) provide some degree of evaluation of various properties of a coated surface. The most relevant of these methods to the present invention is Test Method D-522 which measures the percent elongation at failure of a coated surface after that surface has been bent 180 degrees around a mandril of known diameter. (It should be noted that "strain" and "percent elongation" are synonymous in this field and the two terms will be used interchangeably in the discussion hereinbelow.) An important characteristic, and, as will appear, disadvantage, of this testing method is that the elastic limit of the substrate material is greatly exceeded at the 180 degree bend.

Another ASTM method, D-2370, measures the strain (percent elongation), at failure, of a free standing sheet of organic coating material. However, the limiting strain in a free-standing sheet is not the same property as the limiting strain of a coated surface.

Other ASTM test methods of background interest include the following: D-4145, which is entitled "Coating Flexibility of Prepared Sheet" and is not a quantitative test; D-3281 which is entitled "Formability of Attached Coatings" and which measures the distance of adhesive failure; D-4146, which is entitled "Formability of Complex Coatings on Steel" and which does not provide a quantitative test; D-4541, which is entitled "Adhesion Pull-Off Strength of Coatings" and which measures the stress perpendicular to the surface and requires an adhesive; D-2197, which is entitled "Adhesion of Organic Coatings by Scrape Adhesion" and which provides a relative test and does not measure strain; and D-3359, which is entitled "Adhesion by Tap Test" and which also provides a relative test and does not measure strain.

In general, the techniques used in the prior art for measuring the strain in a coated surface are designed or intended to work only at room temperature. Further, such techniques are dependent on temperature, the material of the substrate, or both.

More specifically, referring particularly to the ASTM Method D-522, this testing method, as indicated above, does not operate within the elastic limit of the substrate and because engineers do not design structures that operate beyond the elastic limit, it is unrealistic to test a coating by deforming a substrate coated with the coating beyond its elastic limit. Further, the mode of deformation used in this testing method is not real and the interaction of the coating with the substrate is not real, particularly if the substrate cracks open during failure. In addition, the method is very imprecise (insensitive) in making measurements of small strains. Further, the method will not work with brittle substrate materials, such as some of the newer aerospace materials. In addition, the methodology provided under ASTM D-522 does not take the coating through more than one strain cycle.

Other prior art of background interest includes U.S. Pat. Nos. 2,294,897 (Ellis); 2,310,845 (Ellis); 2,724,964 (Singdale); 3,779,065 (Ellis); and 2,645,935 (Pramuk et al). The first four patents relate to methods for determining strain in rigid members wherein a coating of a known maximum strain is applied to a test member, the member is subjected to strain and the crack pattern is observed as the loading is increased. The Pramuk et al patent discloses a method for determining the mechanical properties of cantilever beam of a selected material by loading the beam.

SUMMARY OF THE INVENTION

In accordance with the invention, a testing method and apparatus are provided which overcome the disadvantages of prior art tests such as those discussed above. The method and apparatus of the invention enable the strain in a coated surface to be measured in a simple manner over a very wide range of temperatures (between $-300$ and $+825$ degrees Fahrenheit) and provide a temperature and material independent way to characterize the adhesive and flexibility properties of a coated surface at temperatures over this wide range.

In accordance with a first aspect of the invention, a method is provided for determining the strain developed in a coated surface, wherein the method comprises mounting a beam, with a coating on one surface thereof, as a cantilever with one end of the beam fixed and the other end thereof free and unsupported; applying a force to the free end of the beam to cause deflection of the beam until the coating on the beam fails; and determining the strain in the beam, and hence in the coated surface, at the point of coating failure, based on the dimensions of the beam, the point along the beam where failure of the coating occurs and the amount of deflection of the beam, and independently of the temperature of the beam and the material from which the beam is made.

In a specific embodiment, the determination of strain is made based on the equation $E=1.5hdx/l^3$ where $E$ is strain, $h$ is the thickness of the beam, $d$ is the amount of deflection of the beam, $x$ is the distance from the free end of the beam to the point where failure of the coating occurred, and $l$ is the length of the beam.

Advantageously, the force is applied by a rod member in engagement with the free end of the coated beam. Preferably, the rod member is disposed so as to initially extend perpendicular to the beam and the amount of movement of the rod is measured to determine the amount of deflection of the beam.

In accordance with a further aspect of the invention, an apparatus is provided for measuring the strain developed in a coated surface, the apparatus comprising a beam, having a coating on one surface thereof, mounted as a cantilever with one end thereof supported and the other, free end thereof unsupported; means for providing controlled deflection of the free end of the beam until failure of the coating occurs so that the strain in the beam at the point of failure of the coating can be determined based on the dimensions of the beam, the amount of deflection of the beam when failure of the coating occurs, and the location along the beam at which the failure of the coating occurs, and mean for measuring the amount of deflection of the beam when failure of the coating occurs.

The deflection providing means preferably comprises a rod inserted in said free end of said beam and an actuator for providing upward or downward movement of said rod.

Advantageously, the apparatus further comprises means for varying the temperature of the beam so as to permit strain to be determined at different temperatures within a temperature range. In an advantageous embodiment, the apparatus further comprises a container in which the beam is supported and a coolant, contained within the container, in which the beam is immersed. Preferably, the apparatus further includes heating means for providing controlled heating of the beam. This heating means advantageously comprises a heat sensor for sensing the temperature of the beam and a heater responsive to the heat sensor for maintaining the temperature of the beam at a preselected value within the range set by the lowest temperature of the coolant and the highest temperature of the heater.

Other features and advantages of the invention will be set forth in, or apparent from, the following detailed description of preferred embodiments of the invention.

DETAILED DESCRIPTION OF THE INVENTION

Figure 1:
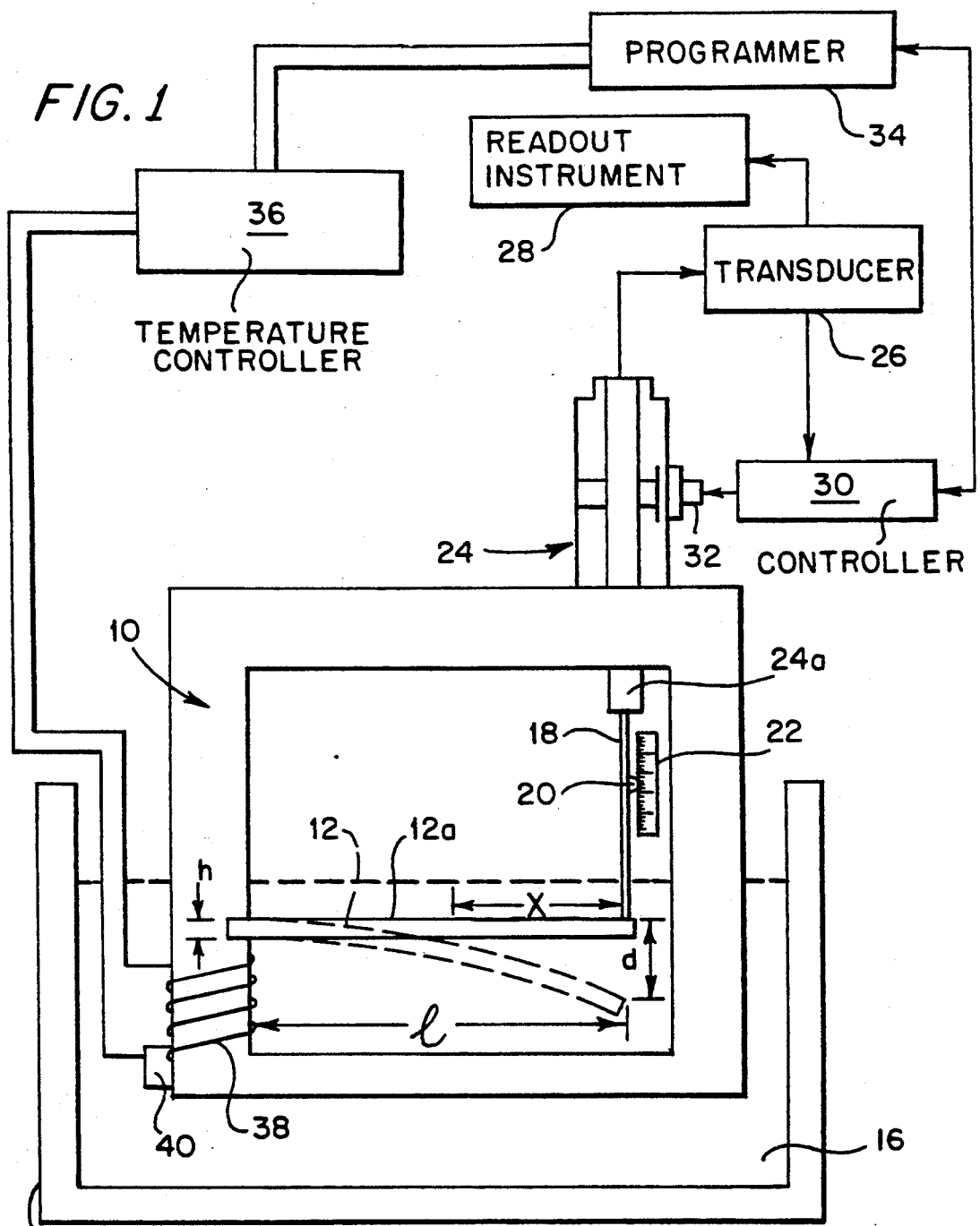
FIG. 1 is a schematic side elevational view, partially in block form, of a strain measuring apparatus in accordance with a preferred embodiment of the invention.

Referring to FIG. 1, a test apparatus constructed in accordance with a preferred embodiment of the invention is shown. The apparatus includes a box-like jig 10 which clamps in place a coated cantilever beam 12 under test. As illustrated, beam 12 includes a coating 12a on the upper surface thereof. The jig 10 is supported in an open styrofoam container 14 which contains a liquid coolant or cryoge indicated at 16. With this arrangement, the beam 12 can be completely immersed in the coolant or cryogen 16.

A vertically extending rod 18 is inserted in a detent or aperture in the free end of beam 12. In this embodiment, rod 18 carries a pointer 20 that cooperates with a scale 22 which can be supported by jig 10. A hydraulic actuator 24 mounted on jig 10 includes a piston 24a which is adapted to engage the upper, free end of rod 18 and to cause downward movement of the rod 18, thereby causing deflection on the free end of the coated beam 12. It will be understood that the coating can be provided on either the upper or the lower surface of the beam and that in the latter case the direction of deflection would be upwards. In one case, the coating is compressive strain and in the other, the coating is in tensile strain.

Actuator 24 is preferably controlled by a servosystem including a transducer 26 which measures the displacement of the actuator piston 24a and provides an output to a readout instrument 28 and to a controller 30. The latter controls the operation of a servovalve 32 associated with hydraulic actuator 24 so as to ensure that the desired displacement of piston 24a is achieved. A programmer 34 can be used to control the operation of controller 30 as well as that of a temperature controller 36 connected to a heating coil 38 wrapped around the clamping end of jig 10, as shown. A temperature sensor 40 mounted on jig 10 is connected to temperature controller 36 so as to provide an indication of the temperature of jig 10. By appropriate adjustment of the electrical heating (as provided by coil 38) and cryogenic cooling, the temperature of the beam 12 can be closely controlled as well as varied over a wide range.

Figure 2:
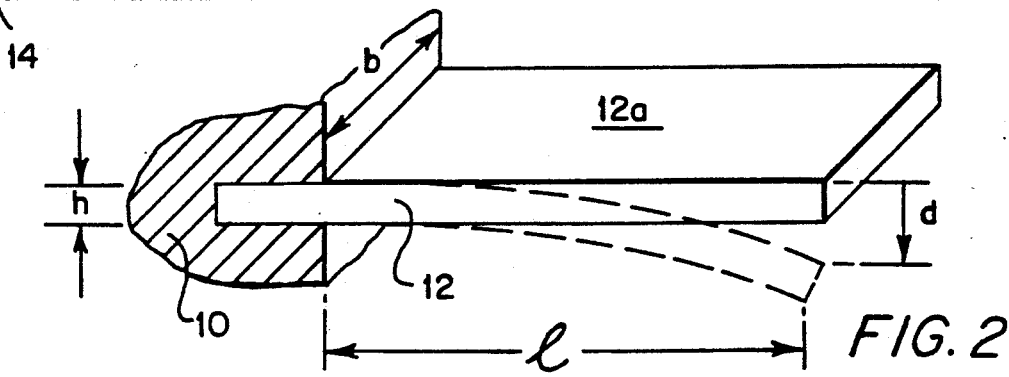
FIG. 2 is a perspective view of the cantilever of FIG. 1.

The coated cantilever beam 12, which can be seen more clearly in FIG. 2, has representative dimensions as shown, i.e., a length l, a thickness or height h, and a width b, while the downward deflection of the free end of beam 12 provided by hydraulic actuator 24 is denoted d. The strain in the coating 12a is the same as the strain at the upper surface of beam 12 until the coating 12a fails, i.e., until coating 12a separates in some way from the beam 12. The place or location at which coating 12a first fails is measured from the free end of beam 12 and is denoted x in FIGS. 1 and 2. It has been shown experimentally (and can be shown theoretically) that the strain, E, in the beam 12, and hence the strain in the coating 12a, at the point of failure, is given by the equation:

$$E = 1.5hdx/l^3$$

where h, d, x and l are the quantities defined above and as indicated in FIGS. 1 and 2.

It is important to note that this equation is independent of the elastic modulus of the material of the beam 12 and therefore, independent of both the temperature and the kind of material from which the beam is made. The equation assumes that the strain developed in the beam 12 remains below the elastic limit of the substrate material (which, as discussed above, is consistent with the structural designs of engineers in any event).

Considering the equation set forth above in a different way, what the equation says is that strain at the interface of the coating and the beam surface depends only on the macroscopic dimensions h, d, x and l and hence is, as stated, independent of the kind of substrate material and the temperature thereof. However, important characteristics of the coating, such as the flexibility and brittleness thereof and the adhesion thereof to the substrate do, in fact, depend on temperature and thus by bending the beam to the point of coating failure, the maximum or limiting strain which the coated beam can sustain at that temperature is measured and this measurement, it is important to appreciate, is independent of any temperature effects that might be introduced by the measurement apparatus. Therefore, characterizing the adhesion or flexibility of a coated beam by the limiting strain (as determined above) at temperatures between −300 and +825 degrees Fahrenheit is accomplished by a direct, absolute, measurement, which is independent of instrumentation effects that could be due to the temperature of the apparatus itself.

An additional feature of the invention is that because the strain is independent of the material from which the beam is made, the method and apparatus of the invention can be used to quantitatively test the adhesion of a coating to many different kinds of materials.

Although the present invention has been described relative to specific exemplary embodiments thereof, it will be understood by those skilled in the art that variations and modifications can be effected in these exemplary embodiments without departing from the scope and spirit of the invention.

What is claimed is:

1. A method of determining the strain developed in a coated surface, said method comprising:
   mounting a beam, with a coating on a surface thereof, as a cantilever with one end of the beam fixed and the other end thereof free and unsupported;
   applying a force to the free end of the beam to cause deflection of the beam until the coating on the beam fails; and
   determining the strain in the beam, and hence in the coating at the point of failure, based on the dimensions of the beam, the point along the beam where failure of the coating occurs and the amount of deflection of the beam, independently of the temperature of the beam and the material from which the beam is made.

2. A method as claimed in claim 1 wherein the determination of strain is made based on the equation $E = 1.5hdx/l^3$ where E is strain, h is the thickness of the beam, d is the amount of deflection of the beam, x is the distance from the free end of the beam to the point where failure of the coating occurred, and l is the length of the beam.

3. A method as claimed in claim 1 wherein said downward force is applied by a rod member in engagement with the free end of the coated beam.

4. A method as claimed in claim 3, wherein said rod member is disposed so as to extend perpendicular to said beam and the amount of movement of the rod is measured to determine the amount of deflection of the beam.

5. A method of determining the maximum strain developed in a coated surface, said method comprising the steps of:
   providing a cantilevered beam having a coating on the upper surface thereof, said beam having a supported end and a free end;
   applying a controlled downward force to the upper surface of the beam at the free end of the beam so as to cause downward deflection of said free end until there is a failure of the coating on the beam; and
   determining the limiting strain which the coating can sustain based on the thickness and length of the beam, the location along the beam at which failure of the coating occurs and the amount of deflection of the beam when failure of the coating occurs, and independently of the temperature of the beam and the material from which the beam is made.

6. The method as claimed in claim 5 wherein the determination of strain is made based on the equation $E = 1.5hdx/l^3$ where E is strain, h is the thickness of the beam, d is the amount of deflection of the beam, x is the distance from the free end of the beam to the point where failure of the coating occurred, and l is the length of the beam.

7. A method as claimed in claim 5 wherein said downward force is applied by a rod member in engagement with the free end of the coated beam, said rod member being disposed so as to extend perpendicular to said beam, and wherein, the amount of movement of the rod is measured to determine the amount of deflection of the beam.

* * * * *